(12) United States Patent
Matsumoto et al.

(10) Patent No.: US 9,717,884 B2
(45) Date of Patent: Aug. 1, 2017

(54) CATHETER

(71) Applicant: ASAHI INTECC CO., LTD., Nagoya-shi, Aichi (JP)

(72) Inventors: Satoru Matsumoto, Kasugai (JP); Takayuki Hori, Owariasahi (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 0 days.

(21) Appl. No.: 15/042,303

(22) Filed: Feb. 12, 2016

(65) Prior Publication Data

US 2016/0235941 A1   Aug. 18, 2016

(30) Foreign Application Priority Data

Feb. 13, 2015  (JP) ................................. 2015-026948
Dec. 11, 2015  (JP) ................................. 2015-242283

(51) Int. Cl.
*A61M 25/00*   (2006.01)
*A61M 25/01*   (2006.01)

(52) U.S. Cl.
CPC ...... *A61M 25/005* (2013.01); *A61M 25/0026* (2013.01); *A61M 25/0045* (2013.01); *A61M 25/0108* (2013.01); *A61M 25/0012* (2013.01); *A61M 2025/0039* (2013.01); *A61M 2025/0059* (2013.01)

(58) Field of Classification Search
CPC ............ A61M 25/005; A61M 25/0045; A61M 25/0053; A61M 25/0012; A61M 25/0026; A61M 25/0108; A61M 2025/0039
See application file for complete search history.

(56) References Cited

U.S. PATENT DOCUMENTS

| | | | |
|---|---|---|---|
| 5,253,653 A | 10/1993 | Daigle et al. | |
| 5,810,837 A * | 9/1998 | Hofmann | A61F 2/88 606/108 |
| 5,906,606 A * | 5/1999 | Chee | A61M 25/005 604/246 |
| 6,723,113 B1 * | 4/2004 | Shkolnik | A61M 25/1025 604/103 |

(Continued)

FOREIGN PATENT DOCUMENTS

| | | | | |
|---|---|---|---|---|
| CA | WO 2013179103 A1 * | 12/2013 | ............. | A61B 5/064 |
| EP | 0033659 A2 | 8/1981 | | |

(Continued)

OTHER PUBLICATIONS

Jul. 14, 2016 Extended European Search Report issued in European Application No. 16153562.0.

*Primary Examiner* — Kami A Bosworth
*Assistant Examiner* — Alexandra Lalonde
(74) *Attorney, Agent, or Firm* — Oliff PLC

(57) ABSTRACT

A catheter that prevents excessive concentration of stress while providing sufficient flexibility to a distal end portion of the catheter, even when the catheter is inserted and curved in patient's a blood vessel. Thus, breakage of the catheter at a radiopaque marker is prevented/reduced. The catheter includes a catheter tube and the radiopaque marker, which is disposed in the catheter tube. The radiopaque marker is fixed in the catheter so that a gap is provided between the radiopaque marker and the catheter tube in a radial direction of the catheter tube.

2 Claims, 6 Drawing Sheets

(56) References Cited

U.S. PATENT DOCUMENTS

| | | | |
|---|---|---|---|
| 8,157,790 B2* | 4/2012 | Kubo | A61M 25/0045 |
| | | | 604/526 |
| 2003/0125711 A1 | 7/2003 | Eidenschink et al. | |
| 2006/0201601 A1 | 9/2006 | Furst et al. | |
| 2015/0314108 A1* | 11/2015 | Kanemasa | A61M 25/0144 |
| | | | 604/95.04 |

FOREIGN PATENT DOCUMENTS

| | | | | |
|---|---|---|---|---|
| JP | S64-68276 A | 3/1989 | | |
| JP | 2006-034347 A | 2/2006 | | |
| JP | 2009-268648 A | 11/2009 | | |
| JP | 2012196275 A | 10/2012 | | |
| JP | WO 2014098020 A1 * | 6/2014 | | A61M 25/0144 |
| WO | 01/62331 A1 | 8/2001 | | |
| WO | 2013/179103 A1 | 12/2013 | | |

\* cited by examiner

CATHETER

CROSS REFERENCE TO RELATED APPLICATION

This application claims priority to Japanese Patent Application No. 2015-242283, filed in the Japan Patent Office on Dec. 11, 2015, and Japanese Patent Application No. 2015-026948, filed in the Japan Patent Office on Feb. 13, 2015, the entire contents of which are incorporated by reference.

BACKGROUND

The disclosed embodiments relate to a catheter for medical use.

Conventional balloon catheters include a radiopaque marker at a distal end of the catheter so that a distal end position of the catheter can be visually observed during procedures.

For example, Patent Literature 1 (identified below) discloses a catheter including an elongate main tubular body 10 with a polytetrafluoroethylene core 16 and a polyurethane outer jacket 18, which covers the polytetrafluoroethylene core 16. Additionally, the catheter includes a soft pointed tip 12 adhered to a distal end of the main tubular body 10, and a radiopaque precious metal marker band 14 is provided at a portion where the main tubular body 10 and the soft pointed tip 12 are connected to each other (see the upper right column in page 5, FIG. 1, etc.).

Patent Literature 2 (identified below) discloses a catheter tube for medical use that includes a resin inner layer tube, a reinforcing material layer that is wound around the periphery of the inner layer tube, and an outer layer tube that covers the inner layer tube and the reinforcing material layer. Additionally, the catheter tube includes an X-ray impermeable marker that is arranged to be in contact with the reinforcing material layer (see FIG. 20, etc.).

PATENT LITERATURE

Patent Literature 1: Japanese Patent Application Laid-open No. S64-68276
Patent Literature 2: Japanese Patent Application Laid-open No. 2006-34347

SUMMARY

However, the above-described conventional catheters, including the catheters of Patent Literature 1 and Patent Literature 2, have a problem in that the rigidity is much higher in the region where the radiopaque marker is provided than the rigidity of other regions.

To be more specific, the distal end portion of the conventional catheters are formed of resin having high flexibility to facilitate insertion of the catheters into a patient's body. However, when a radiopaque marker formed of metal materials, such as platinum, is provided at the distal end portion of the catheter, the rigidity of the distal end portion becomes higher. This causes a break in rigidity at a border area between the portion where the radiopaque marker is provided and a portion where the radiopaque marker is not provided. Therefore, when a technician operates the conventional catheters such that the catheters are curved repeatedly in a patient's body, for example, stress is excessively concentrated at the border area between the portion where the radiopaque marker is provided and the portion where the radiopaque marker is not provided, causing a problem that the catheters are easily broken at such a border area.

Thus, the present disclosure provides a catheter with a radiopaque marker and that prevents excessive concentration of stress while providing sufficient flexibility to a distal end portion of the catheter, even when the catheter is inserted and curved in a blood vessel. Thus, a break in the catheter due to the radiopaque marker is prevented/reduced.

The disclosed embodiments include a catheter having a tubular body including an inner layer and a distal end outer layer and a ring-formed radiopaque marker disposed in the tubular body, the ring-formed radiopaque marker is disposed between the inner layer and a radially outer portion of the distal end outer layer. A first gap including empty space is provided between the radiopaque marker and the tubular body in a radial direction of the tubular body, the first gap being formed between a radially inner side of the ring-formed radiopaque marker and the inner layer. A radially inner portion of the distal end outer layer partially enters the first gap so that the distal end outer layer extends partialy between the ring-formed radiopaque marker and the inner layer.

In the disclosed embodiments, even when the catheter is inserted and curved in a patient's blood vessel, it is possible to prevent excessive concentration of stress while providing sufficient flexibility to the distal end portion of the catheter. Thus, the disclosed embodiments prevent/reduce breaking of the catheter.

In some embodiments, a second gap is provided on a radially outer side of the radiopaque marker in the radial direction of the tubular body.

In some embodiments, a reinforcing member is disposed in the tubular body such that the reinforcing member extends along a longitudinal axis of the tubular body, the radiopaque marker being fixed to a distal end of the reinforcing member.

In some embodiments, the gap extends at the distal end of the reinforcing member to which the radiopaque marker is fixed.

DETAILED DESCRIPTION OF EMBODIMENTS

The catheter according to the disclosed embodiments will be described with reference to the enclosed drawings. The present disclosure shall not be limited to the embodiments provided below, and modifications in design can appropriately be made.

Figure 1:
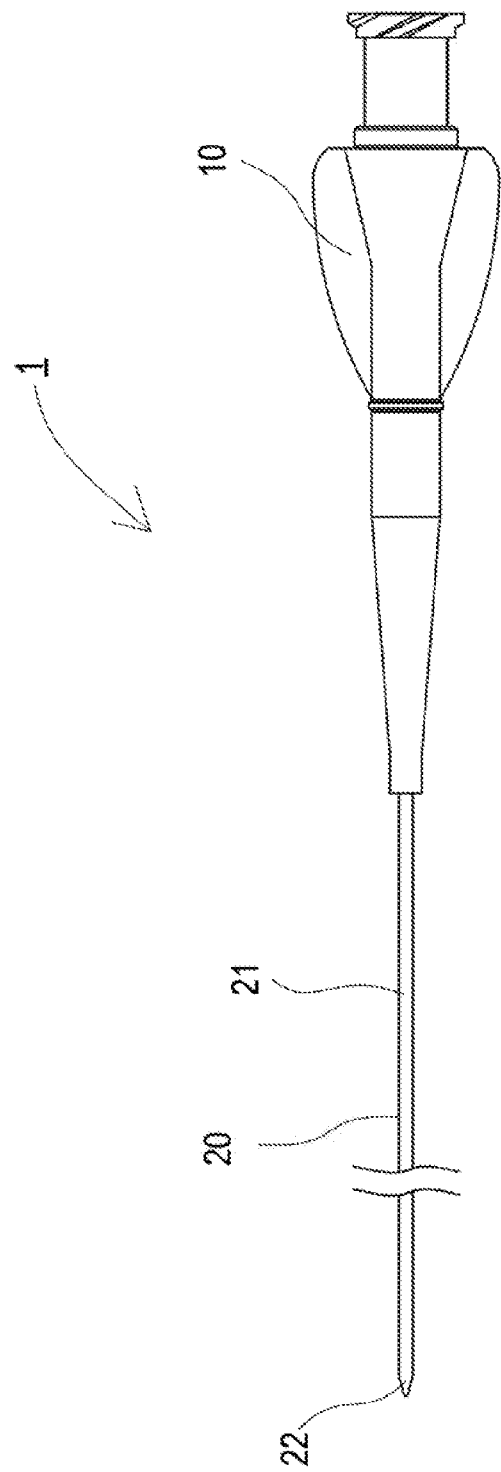
FIG. 1 is a plan view of a catheter according to the disclosed embodiments.
Figure 2:
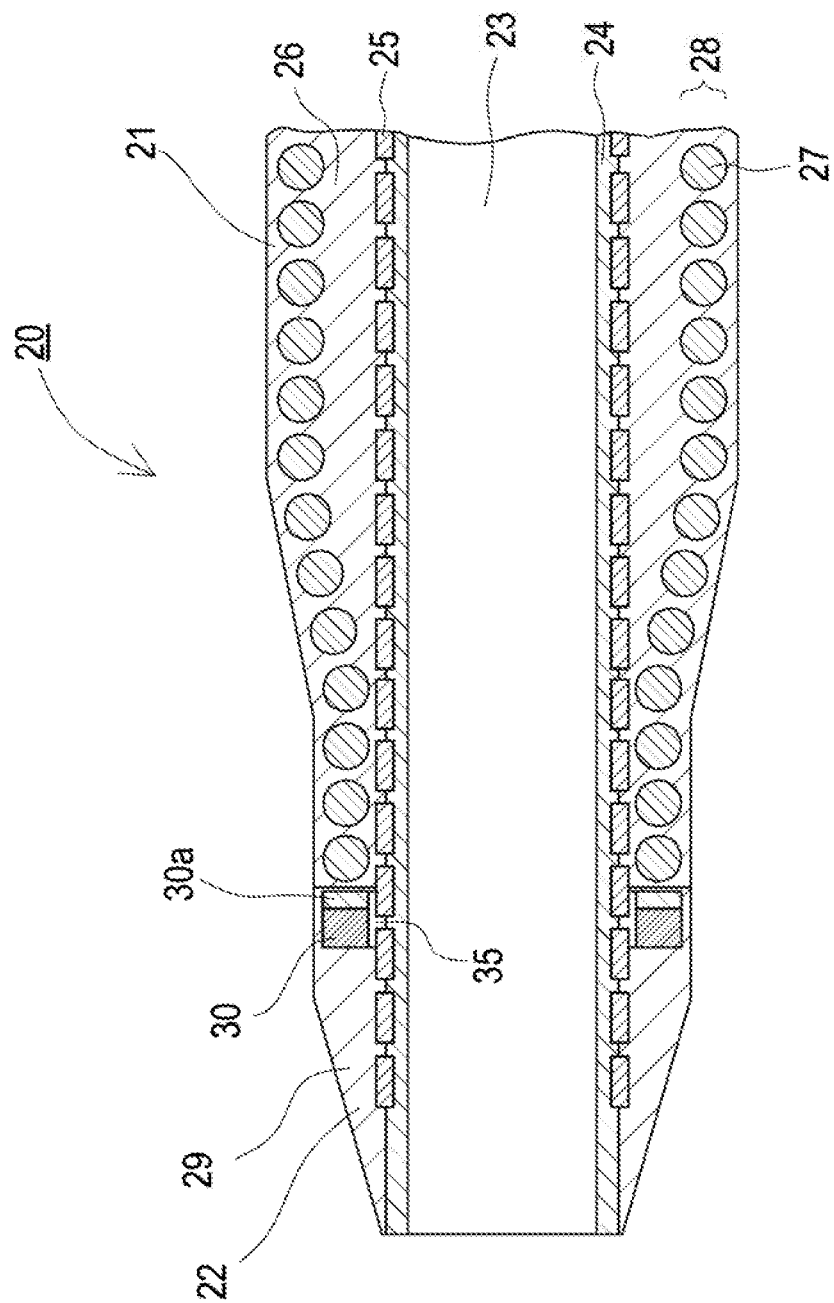
FIG. 2 is a partial enlarged section of the catheter of FIG. 1. according to the disclosed embodiments.

FIG. 1 is a plan view of a catheter according to embodiments of the present disclosure, and FIG. 2 is a partial enlarged section of the catheter of FIG. 1.

As illustrated in FIG. 1, catheter 1 includes an operation part 10, which is operated by a technician, and a catheter tube 20 (corresponding to a "tubular body"), which is connected to a distal end of the operation part 10. Moreover, the catheter tube 20 includes a catheter main body part 21, extending from the operation part 10, and a distal end tip 22, positioned on the distal end side of the catheter main body part 21. Each of the vicinity of the distal end of the catheter main body part 21 and the vicinity of the distal end of the distal end tip 22 has a tapered form in which the outer diameter becomes smaller toward the distal end.

Moreover, as illustrated in FIG. 2, the catheter main body part 21 has a multilayer structure, and includes an inner layer 24, a braid 25, and an outer layer 26 in the order from the inner side in a radial direction relative to a center axis of the catheter main body part 21.

The inner layer 24 has a tubular form with a lumen 23, and the inner layer 24 extends along the catheter main body 21 and along the distal end tip 22. The inner layer 24 is preferably formed of a fluororesin, such as polytetrafluoroethylene, having small sliding resistance. Moreover, the inner layer 24 may have a multilayer structure partially or entirely along its length.

The braid 25 is arranged at the periphery of the inner layer 24. The distal end of the braid 25 is arranged in the distal end tip 22, and the distal end of the braid 25 is proximal of the distal end of the inner layer 24. The braid 25 may be formed of a plurality of pieces of element wire arranged at the periphery of the inner layer 24. Alternatively, the braid 25 may be formed of a coil wound by a single piece or a plurality of pieces of element wire. The braid 25 may be formed of materials such as, for example, stainless steel, superelastic alloy such as an Ni—Ti alloy, piano wire, or tungsten wire.

The outer layer 26 is arranged to cover the periphery of the inner layer 24 and the braid 25. As shown in FIG. 2, the distal end of the outer layer 26 forms the distal end of the catheter main body part 21. A reinforcing member 27, formed of a coil, may be arranged in the outer layer 26 such that the reinforcing member 27 is coaxial with the outer layer 26. Thus, the reinforcing member 27 and the outer layer 26 form a reinforcing layer 28. As shown in FIG. 2, the distal end of the reinforcing member 27 may extend to the distal end of the catheter main body part 21. In the embodiment of FIG. 2, a coil is used as the reinforcing member 27. However, a braid formed by braiding a plurality of pieces of element wire may be used. The reinforcing member 27 is farmed of materials such as, for example, stainless steel, superelastic alloy such as an Ni—Ti alloy, piano wire, or tungsten wire.

The resin materials forming the outer layer 26 may include polyamide, polyamide elastomer, polyester, polyurethane, or the like, for example. In the embodiment of FIG. 2, polyurethane is used. Moreover, the outer layer 26 may have a multilayer structure partially or entirely along its length.

The distal end tip 22 has a multilayer structure, and includes, from the inner side in a radial direction relative to a center axis line of the distal end tip 22, the inner layer 24, the braid 25, and a distal end outer layer 29. The distal end outer layer 29 may be formed continuously from the outer layer 26. The resin materials forming the distal end outer layer 29 may include polyamide, polyamide elastomer, polyester, polyurethane, or the like, for example, similar to the outer layer 26. In the embodiment of FIG. 2, polyurethane is used for the distal end outer layer 29. Thus, the main part of the distal end tip 22 is formed of polyurethane (or the other resin materials disclosed herein) and damage to a patient's blood vessel inner walls can be prevented. In order to improve the visibility of the distal end tip 22, the distal end outer layer 29 preferably contains radiopaque tungsten powder, and the like.

A ring-formed radiopaque marker 30 formed of a platinum material is arranged in the distal end tip 22. The proximal end of the radiopaque marker 30 is fixed to the distal end of the reinforcing member 27 through a fused part 30a. For example, the proximal end of the radiopaque marker 30 and the distal end of the reinforcing member 27 are fused together by YAG welding. In the disclosed embodiments, platinum is used for the radiopaque marker 30. However, other well-known radiopaque metal materials may be used. As shown in FIG. 2, the proximal end of the radiopaque marker 30 and the distal end of the reinforcing member 27 are fused together. However, they may be fixed to each other by other well-known fixing methods, such as an adhesive.

A gap 35 is provided between the inner layer 24 and the radiopaque marker 30 on the inner side in a radial direction of the catheter tube 20. A part of the inner peripheral surface of the radiopaque marker 30 is exposed to the gap 35. That is, an inner peripheral surface of the radiopaque marker 30 that faces the inner layer 24 is not in contact with other members.

In the catheter 1, the radiopaque marker 30 is fixed so that the gap 35 is provided between the radiopaque marker 30 and the inner layer 24 on the inner side in a radial direction of the catheter tube 20. Thus, even when the catheter 1 is inserted and curved in a blood vessel, the gap 35 can sufficiently absorb deformation of the inner layer 24, the distal end outer layer 29, and the like around the radiopaque marker 30. Thus, the gap 35 can prevent excessive concentration of stress. In this manner, it is possible to provide sufficient flexibility to the distal end portion of the catheter 1 while preventing/reducing a break of the catheter 1 at the location (vicinity) of the radiopaque marker 30.

Furthermore, as described above, the radiopaque marker 30 is fused with the distal end of the reinforcing member 27. Thus, it is possible to prevent displacement of the radiopaque marker 30 and excessive concentration of stress. Accordingly, breakage of the catheter at the location (vicinity) of the radiopaque marker 30 is prevented/reduced. Moreover, in the process for manufacturing the catheter tube 20, the distal end outer layer 29 can be formed in the state where the radiopaque marker 30 is fused with the distal end of the reinforcing member 27. Thus, it is possible to prevent displacement of the radiopaque marker 30 and to produce the catheter 1 with high dimensional accuracy.

Furthermore, the reinforcing member 27 and the radiopaque marker 30 are fused with each other so that the resin material forming the distal end outer layer 29 does not enter the gap 35. Thus, it is possible to form the gap 35 easily.

Moreover, the gap 35 is also formed between the fused part 30a (distal end of the reinforcing member 27) and the inner layer 24. Thus, when the catheter 1 is inserted and curved in a patient's blood vessel, it is possible to further prevent excessive concentration of stress. Thus, the distal end portion of the catheter 1 may have sufficient flexibility while preventing/reducing a break of the catheter at the location (vicinity) of the radiopaque marker 30.

Figure 3:
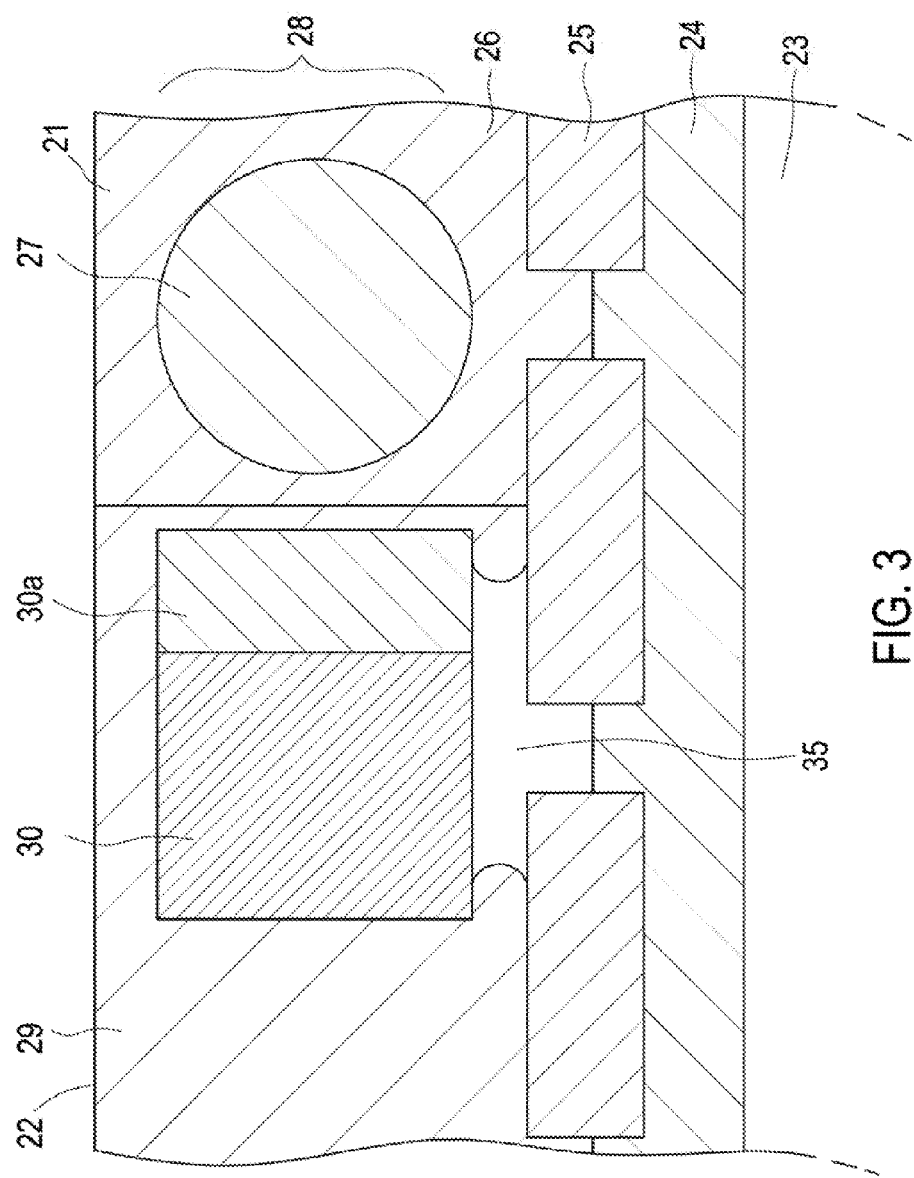
FIG. 3 is a partial enlarged section of the catheter of FIG. 1 according to the disclosed embodiments.

FIG. 3 is a partial enlarged section illustrating a modification of the catheter of FIG. 2. In FIG. 3, the distal end outer layer 29 partially enters the gap 35 provided between the radiopaque marker 30 and the inner layer 24. Thus, the distal end outer layer 29 extends partially between the radiopaque marker 30 and the inner layer 24. In such a configuration, the radiopaque marker 30 is fused with the reinforcing member 27 through the fused part 30a. Additionally, the lower side (inner side) of the radiopaque marker 30 is supported by the distal end outer layer 29. Thus, displacement of the radiopaque marker 30 is further prevented.

As discussed above, the radiopaque marker 30 and the gap 35 are arranged in the tubular body 20 so that the radiopaque marker 30 is fixed in a radial direction of the tubular body 20.

Figure 4:
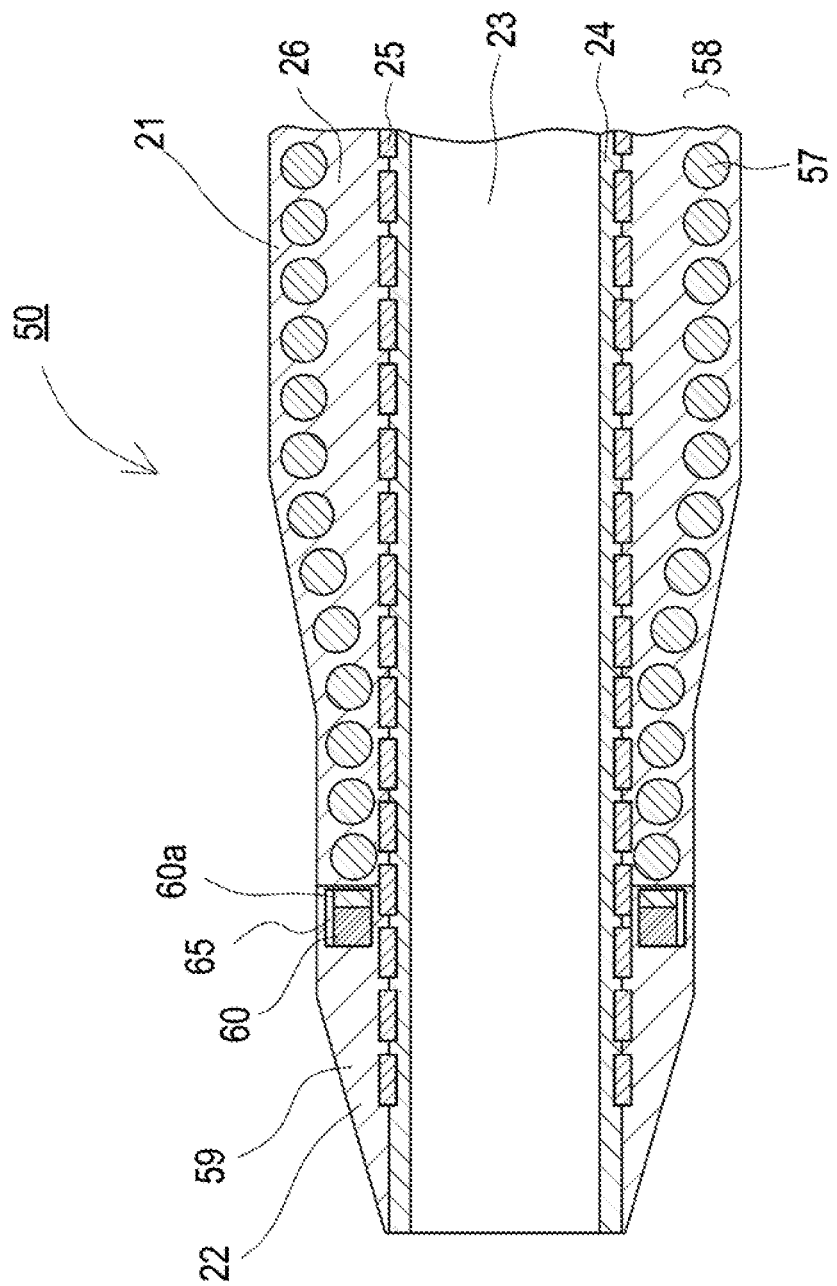
FIG. 4 is a partial enlarged section of the catheter of FIG. 1 according to the disclosed embodiments.

FIG. 4 is a partial enlarged section illustrating a modification of the catheter of FIG. 2. The parts common to the catheter according to the embodiment of FIG. 2 will be represented with the same symbols in the drawings, and the explanation thereof will be simplified or omitted.

In FIG. 4, catheter tube 50 is different from the catheter tube 20 of FIG. 2 in the positional relation between the radiopaque marker and the gap.

Similar to FIG. 2, a radiopaque marker 60 is arranged on the distal end tip 22 such that a proximal end of the radiopaque marker 60 is fused with a distal end of a reinforcing member 57 through a fused part 60a. Additionally, the outer layer 26 and the reinforcing member 57 form a reinforcing layer 58. Distinct from FIG. 2, a gap 65 is arranged on the outer side in a radial direction of the catheter tube 50 relative to the radiopaque marker 60 (between the radiopaque marker 60 and a distal end outer layer 59).

In such a configuration, when the catheter of FIG. 4 is inserted and curved in a patient's blood vessel, it is possible to prevent excessive concentration of stress and to provide sufficient flexibility to the distal end portion of the catheter 1. Thus, it is possible to prevent/reduce a break of the catheter 1 at the location (vicinity) of the radiopaque marker 60. Moreover, the gap 65 is also formed between the fused part 60a (distal end of the reinforcing member 57) and the distal end outer layer 59. Thus, when the catheter is inserted and curved in a patient's blood vessel, it is possible to further prevent excessive concentration of stress and to provide sufficient flexibility to the distal end portion of the catheter. Thus, it is possible to further prevent/reduce a break of the catheter 1 at the location (vicinity) of the radiopaque marker 60.

Figure 5:
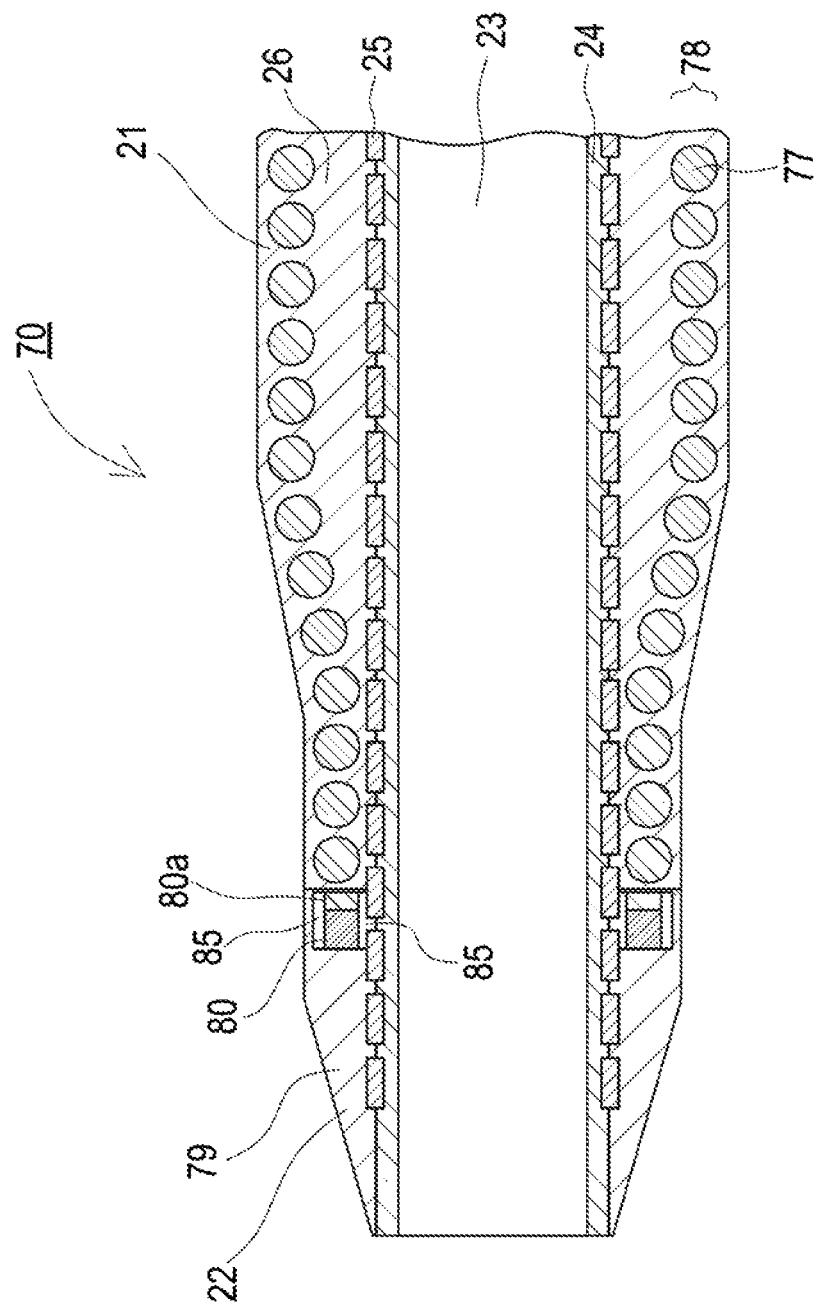
FIG. 5 is a partial enlarged section of the catheter of FIG. 1 according to the disclosed embodiments.

FIG. 5 is a partial enlarged section illustrating a modification of the catheter of FIG. 2. The parts common to the catheter according to FIG. 2 will be represented with the same symbols in the drawings, and the explanation thereof will be simplified or omitted.

In FIG. 5, catheter tube 70 is different from the catheter tube 20 of FIG. 2 in the positional relation between the radiopaque marker and the gap.

Similar to FIG. 2, a radiopaque marker 80 is arranged at the distal end tip 22 such that a proximal end of the radiopaque marker 80 is fused with a distal end of a reinforcing member 77 through a fused part 80a. Additionally, the outer layer 26 and the reinforcing member 77 form a reinforcing layer 78. Distinct from FIG. 2, a gap 85 is arranged on the both sides in a radial direction of the catheter tube 70 relative to the radiopaque marker 80 (between the radiopaque marker 80 and the inner layer 24 and between the radiopaque marker 80 and a distal end outer layer 79).

In such a configuration, when the catheter of FIG. 5 is inserted and curved in a patient's blood vessel, it is possible to further prevent excessive concentration of stress and to provide sufficient flexibility to the distal end portion of the catheter. Thus, it is possible to prevent/reduce a break of the catheter 1 at the location (vicinity) of the radiopaque marker 80.

Figure 6:
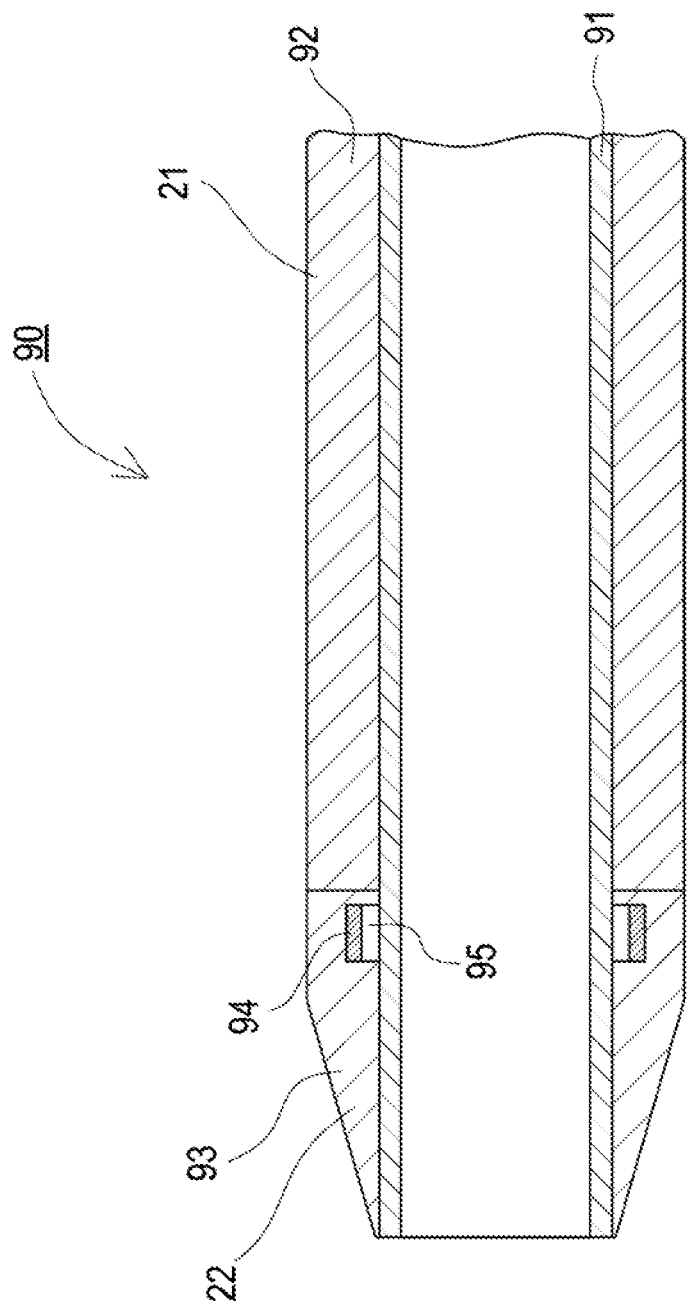
FIG. 6 is a partial enlarged section of the catheter of FIG. 1 according to the disclosed embodiments.

FIG. 6 is a partial enlarged section illustrating a modification of the catheter of FIG. 2. The parts common to the catheter according to FIG. 2 will be represented with the same symbols in the drawings, and the explanation thereof will be simplified or omitted.

Similar to FIG. 2, catheter tube 90 includes the catheter main body part 21 and the distal end tip 22. The catheter main body part 21 includes an inner layer 91 and an outer layer 92, covering the periphery of the inner layer 91. The distal end tip 22 includes the inner layer 91, which extends from the catheter main body part 21, and a distal end outer layer 93, which covers the periphery of the inner layer 91.

A radiopaque marker 94 is arranged at the distal end tip 22 between the inner layer 91 and the distal end outer layer 93. Additionally, a gap 95 is provided between the radiopaque marker 94 and the inner layer 91.

In such a configuration, when the catheter is inserted and curved in a patient's blood vessel, it is possible, with the gap 95 on the inner side of the radiopaque marker 94, to prevent excessive concentration of stress and to provide sufficient flexibility to the distal end portion of the catheter 1. Thus, it is possible to prevent/reduce a break of the catheter 1 at the location (vicinity) of the radiopaque marker 94.

The gap 95 is provided between the radiopaque marker 94 and the inner layer 91. However, similarly to the catheters discussed above, the gap 95 may be provided on the outer side in a radial direction of the catheter tube 90 relative to the radiopaque marker 94 (between the radiopaque marker 94 and the distal end outer layer 93) or on the both sides in a radial direction of the catheter tube 90 relative to the radiopaque marker 94 (between the radiopaque marker 94 and the inner layer 91 and between the radiopaque marker 94 and the distal end outer layer 93). Also in such cases, the same effect as the effect described in each embodiment is exerted.

As discussed above, the radiopaque marker may be arranged at the distal end tip 22. Additionally or alternatively, the radiopaque marker may be arranged at the catheter tube 20/50/70/90. In such a case, the same effect as the effect described in each embodiment is exerted.

In some embodiments, the catheter tube 20/50/70/90 and the distal end tip 22 may be formed integrally with each other. In such a case, the same effect as the effect described in each embodiment is exerted.

In the embodiments discussed above, the radiopaque marker has a ring shape. However, the shape of the radiopaque marker may be other shapes such as, for example, a coil shape or a ring shape with a partial cutout.

What is claimed is:

1. A catheter, comprising:
   a tubular body including an inner layer and a distal end outer layer; and
   a ring-formed radiopaque marker disposed in the tubular body,
   wherein the ring-formed radiopaque marker is disposed between the inner layer and a radially outer portion of the distal end outer layer,
   a first gap including an empty space is formed between a radially inner side of the ring-formed radiopaque marker and the inner layer, and
   a radially inner portion of the distal end outer layer partially enters the first gap so that the distal end outer layer extends partially between the ring-formed radiopaque marker and the inner layer.

2. The catheter according to claim 1, wherein a second gap is provided on a radially outer side of the ring-formed radiopaque marker.

\* \* \* \* \*